United States Patent
Chang et al.

(10) Patent No.: US 8,218,927 B2
(45) Date of Patent: Jul. 10, 2012

(54) OPTICAL CATHETER WITH ROTARY OPTICAL CAP

(75) Inventors: Shoude Chang, Ottawa (CA); Erroll Murdock, Ottawa (CA); Costel Flueraru, Ottawa (CA); Youxin Mao, Ottawa (CA)

(73) Assignee: National Research Council of Canada, Ottawa ON ( * ) Notice: Subject to any disclaimer, the term of this patent is extended or adjusted under 35 U.S.C. 154(b) by 30 days.

(21) Appl. No.: 12/662,447

(22) Filed: Apr. 19, 2010

(65) Prior Publication Data

US 2011/0257486 A1    Oct. 20, 2011

(51) Int. Cl.
G02B 6/06 (2006.01)
G01B 9/02 (2006.01)
A61B 1/06 (2006.01)

(52) U.S. Cl. ........ 385/117; 385/115; 385/116; 385/118; 385/119; 600/182; 356/450

(58) Field of Classification Search .......... 385/115–121; 600/477, 566, 182; 356/450
See application file for complete search history.

(56) References Cited

U.S. PATENT DOCUMENTS

| | | | |
|---|---|---|---|
| 6,445,939 B1 | 9/2002 | Swanson et al. | |
| 6,891,984 B2* | 5/2005 | Petersen et al. | 385/12 |
| 7,450,244 B2 | 11/2008 | Xie | |
| 7,853,316 B2 | 12/2010 | Milner et al. | |
| 2008/0243031 A1* | 10/2008 | Seibel et al. | 600/566 |
| 2009/0027689 A1* | 1/2009 | Yun et al. | 356/511 |
| 2009/0042205 A1 | 2/2009 | Didenko | |
| 2009/0073455 A1* | 3/2009 | Onimura | 356/479 |
| 2009/0143686 A1* | 6/2009 | Onimura et al. | 600/477 |

FOREIGN PATENT DOCUMENTS

WO    WO 2007/091991    8/2007

OTHER PUBLICATIONS

Bonnema et al, "A concentric three element radial scanning optical coherence tomography endoscope", J. Biophoton, 2009, vol. 2, No. 6-7, p. 353-536.
Chu Jennifer, "New Endoscope Sees What Lies Beneath", MIT Technology Review, 2009.
Herz et al, "Micromotor endoscope catheter for in vivo, ultrahigh-resolution optical coherence tomography", Optics Letters, 2004, vol. 29, No. 9, p. 2261-2263.
Jung Min et al., "Single-body lensed-fiber scanning probe actuated by magnetic force for optical imaging", Optics Letters, 2009, vol. 34(12), p. 1897-1899.

(Continued)

Primary Examiner — Brian M. Healy
Assistant Examiner — Guy Anderson
(74) Attorney, Agent, or Firm — Jason E. J. Davis

(57) ABSTRACT

A scanning optical head for a catheter is locally controlled by a motor at an insertion end of the catheter uses a hollow motor through which a longitudinal optical path of the catheter passes. This permits the motor to be positioned between a control base of the catheter and avoids rotating the whole fiber, and therefore makes the beam scanning stable and accurate. In addition, because there is no coupling component, it also eliminates the light reflection between additional surfaces as well as varying fiber birefringence, which becomes a cause of noise when imaging the deep structure.

19 Claims, 2 Drawing Sheets

OTHER PUBLICATIONS

Munce et al., "Electrostatic forward-viewing scanning probe for Doppler optical coherence tomography using a dissipative . . . ", Optics Letters, 2008, vol. 33(7), p. 657-659.

New Scale Technologies, Inc.; Website http://www.newscaletech.com.

Outils Mora Tools Inc.; Website http://www.omtmora.com/eng/home.htm.

Petersen et al., "Design of an OCT imaging system for intravascular applications", Optical Coherence Tomography in Cardiovascular . . . , Chapter 1.3, 2007, Informa Healthcare.

Takahashi et al., "Optical probe using eccentric optics for optical coherence tomography", Optics Communications 271, 2007, p. 285-290.

Tower Optical Corporation; Website http://www.toweroptical.com.

Tran et al., "In vivo endoscopic optical coherence tomography by use of a rotational microelectricalmechanical system probe", Optics Letters, 2004, vol. 29(11), p. 1236-1238.

Su et al, "In vivo three-dimensional microelectromechanical endoscope swept source optical coherence tompography", Optics Express, 2007, vol. 5, No. 16, pp. 10390-10396.

J. Wu et al., "Paired-angle-rotation scanning optical coherence tomography forward-imaging probe", Optics Letters, 2006, vol. 31(9), p. 1265-1267.

L. Wu et al, "Electrothermal micromirror with dual-reflective surfaces for circumferential scanning . . . ", J. Micro/Nanolith, MEMS MOEMS, 2009, vol. 8(1), p. 013030-1-013030-7.

Xiaodong et al, "Endoscopic optical coherence tomography system", Proc. of SPIE, 2006, 6357-63574B.

Xu et al, "MEMS based non-rotatory circumferential scanning optical probe for endoscopic optical coherence tomography", Proc. of SPIE-OSA, 2007, vol. 6627-662715-1.

\* cited by examiner

OPTICAL CATHETER WITH ROTARY OPTICAL CAP

FIELD OF THE INVENTION

The present invention relates in general to optical catheters, and, in particular, to an optical catheter with a motorized rotary optical cap for 360° azimuthal scanning of the beam without occlusion of the beam, the catheter design being scalable to outer diameter sizes smaller than 2 mm.

BACKGROUND OF THE INVENTION

Optical catheters are increasingly used for a wide variety of optical diagnostic procedures and interventions. Accessing tissues via blood vessels, or other orifices, as opposed to by open surgery, reduces damage to the body, facilitating recovery. Generally the finer the catheter, the smaller the blood vessel it can enter. The present invention is particularly suited to providing catheters having small diameters and requiring reliable rotation.

A reliable rotary fibre scanner is a critical part of optical coherence tomography (OCT) systems employed for medical imaging and diagnosis, particularly, to intravascular and cardiovascular applications. In particular up to 70% of heart attacks are thought to be caused by vulnerable plaque in arterial walls. OCT systems with rotary fibres may provide a useful tool to image and analyze the plaques.

Most legacy technologies use a rotary motor at a base end of the fibre outside the body, and rotate the whole fibre to perform the circular scan (e.g. U.S. Pat. No. 6,445,939). As the fibre have lengths around 1.5 m, and the fibers are bent and twisted, and subject to different forces in use, the rotation of the base end does not necessarily correspond to equal angular changes at the inserted end of the catheter, and neither stable nor uniform rotary actuation is provided. In application, the rotation at the inserted end of the fibre suffers from non-uniform movements, which directly results in scanning errors during the measurement (non-uniform rotational distortion). Because those errors appear to be random, it is almost impossible to calibrate and compensate them by post-processing. As scanning techniques require higher precision in terms of positioning and momentum of the inserted end, this technique becomes increasingly problematic. Diameters of typically used optical fibre are ~150 µm, it is very difficult to make a part to rotate the laser beam emitted from optical fibre. Furthermore a coupling component which passes the light from a non-rotating fibre to a rotating fibre at the base end has been known to pose problems with losses. Time-varying fibre birefringence may also be a problem with this type of scanning technique. This is a known problem in the art, and various solutions have been proposed. For example, U.S. Pat. No. 6,891,984 teaches provision of a viscous damping fluid located within the sheath to provide drag.

A second technique involves placing the motor at a distal end of the catheter (e.g. "Micromotor endoscope catheter for in vivo, ultrahigh-resolution optical coherence tomography" Herz et al. Optics Letters v. 29, No. 9, Oct. 1, 2004, "In vivo three-dimensional microelectromechanical endoscope swept source optical coherence tomography" Su et al. Optics Express v. 15, No. 16, 10390, Aug. 6, 2007, and "Endoscopic optical coherence tomography system" Xiadong et al. Proc. of SPIE v. 6357, 63574B, 2006). This has disadvantages that power and control wires occlude the sensor over part of the radial scan of the device.

Concentric drive endoscopes are also known ("A concentric three element radial scanning optical coherence tomography endoscope" Bonnema et al. J. Biophoton., 2, No. 6-7, 353-356, 2009), but a concentric drive brings with it severe constrains on the flexibility of the endoscope, and is not suitable for passage through winding blood vessels.

Finally MEMS devices with limited rotation have been designed that avoid the above problems, and place a motor near the distal output of the beam, but between the beam exit and the base end (e.g. "MEMS based non-rotatory circumferential scanning optical probe for endoscopic optical coherence tomography" Xu et al. Proc. of SPIE-OSA, v. 6627, 662715-1, 2007; "New endoscope sees what lies beneath" MIT Tech, Rev., Dec. 3. 2009). However such devices introduce several other difficulties, including the diameter, the complexity of the device, and increased optical insertion loss from multiple reflections, the complexity and cost of forming the device, etc.

As power supplies and electromagnetic actuation are all highly problematic, there are limited possibilities for actuation of catheters.

Accordingly there is a need for a catheter having a motorized rotational control at the insertion end, for higher control, but avoids the problems of wires crossing the scanning beam, and provides a reliable, relatively low cost fabrication, assembly, and use.

SUMMARY OF THE INVENTION

Applicant has conceived and tested a motor drive system for a catheter that consists of a hollow motor that can surround the fibre (or other light path) that extends longitudinally through the catheter.

In accordance with the present invention a catheter is provided, the catheter comprising: an electromagnetic path passing longitudinally through a body of the catheter from a base end to an insertion end; and a motor encircling the longitudinal path at the control end, surrounding the longitudinal path. The motor is anchored to the catheter and has a rotor extending away from the control end, in a direction of the insertion end. The rotor is coupled to an electromagnetic path element that caps the longitudinal path, to redirect a beam between the longitudinal path and a substantially radial direction, in at least one mode of operation.

The path element may be coupled to the catheter via the rotor. The motor may comprise a plurality of actuable piezoelectric elements secured to the anchoring in a ring around the longitudinal path for selectively engaging the rotor, which is in the form of a cylinder concentrically mounted about the ring, or may drive the rotor in a circular or helical motion. The motor may be a squiggle motor.

The electromagnetic path may comprise an optical fibre; such as an optical fiber that extends through the catheter, through the motor, and at least partly into the rotor, and preferably completely through the rotor. The optical fibre may have a lensed tip, and the tip may have a higher OD than a remainder of the optical fibre. The tip may be a colimating lens or a ball lens. The optical fiber may have a protective casing. The optical fiber may be rotatably mounted to the catheter, and may be rotatably mounted to the catheter but retained against longitudinal movement with respect to the catheter, for example at the insertion end, preferably at an inner through bore of the rotor. The optical fibre may be unrestrained with respect to rotation or longitudinal movement of the catheter at the insertion end.

The electromagnetic path element may comprise a deflector, consisting of a reflective, diffractive, or refractive surface. The deflector may consisting of a dichroic mirror for deflecting only some modes along the electromagnetic path. The electromagnetic path element may further include one or more lenses. The deflector may be mounted rigidly to a cap that is affixed to the rotor; or to an optical fibre that provides the longitudinal path.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
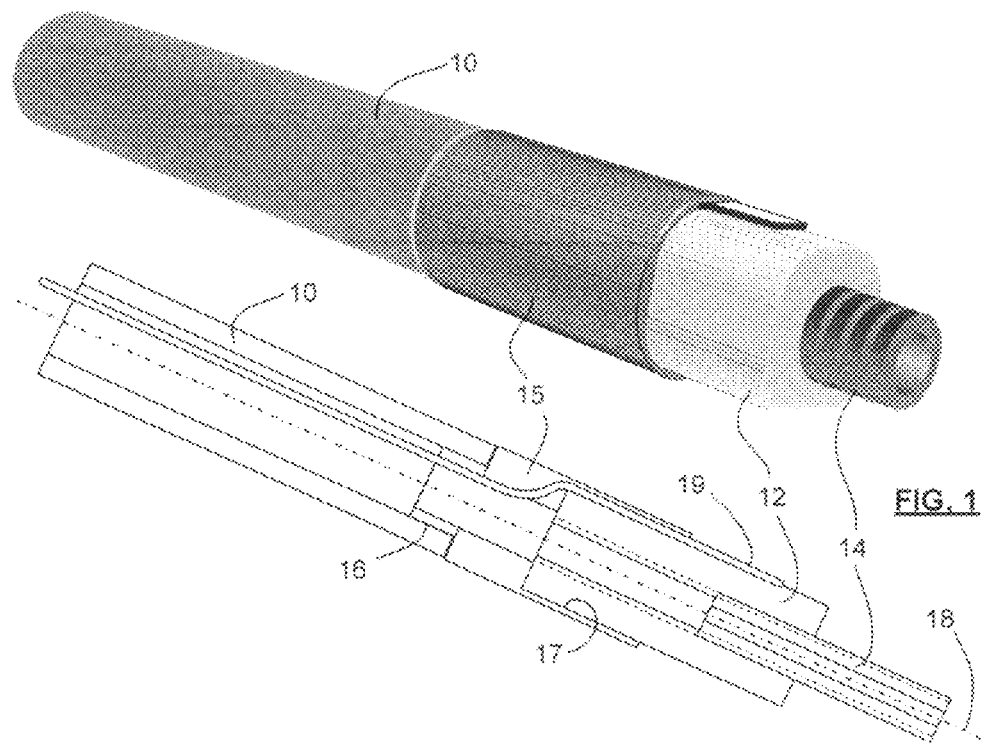
FIG. 1 is a schematic illustration of a catheter in accordance with an embodiment of the invention, having a rotor extending concentrically away from a base of the catheter upon which an electromagnetic path element may be rotationally mounted.

FIG. 1 shows two schematic illustrations of a catheter: on top a perspective drawing, and below a cross-sectional view. The catheter comprises a covering 10 which is secured to motor 12 for driving a pin threaded shaft 14, which is accordingly a rotor. It will be noted that an internal structure of the motor 12 is not shown in the cross-sectional drawing, but that independently controlled pairs of parallel piezoelectric actuators that selectively threadedly engage the pin thread on the shaft 14 may be used, for example as in a squiggle motor. In the illustrated embodiment, motor 12 and covering 10 are coupled by an intermediate part 15, which provides a lip 16 for sealed connection to the covering 10 at a proximal end, and a cavity 17 at the distal end for receiving the motor 12, the motor 12, and covering 10 are glued to the intermediate part 15 at respective ends. The outer surface of motor 12 has a cross-section that is substantially square, with rounded edges, whereas the outer surfaces of the intermediate part 15, and cover 10 (unflexed) are substantially cylindrical, thus a rotational base of support is provided against which the motor 12 acts. This rotational support relies on the covering 10 to have sufficient inertia, even when bent and torsioned, to resist the forces exerted on the shaft 14.

The motor 12 and shaft 14, intermediate part 15, and covering 10 are all hollow, collectively forming throughbore concentric with a longitudinal axis 18. In the embodiment of FIG. 1, leads for power supply and control of motor 12 pass from the outer surface into the throughbore at the intermediate part 15, which throughbore the leads 19 follow to the base of the catheter (not in view). However, it will be appreciated that the leads 19 could be held to an outer surface of the covering 10, or enter the throughbore at any other position. For example a hole can be bored or otherwise provided through the intermediate part 15, or covering 10 at any point for this purpose.

The catheter shown in FIG. 1 has a throughbore that permits definition of an optical path concentric with the longitudinal axis 18 in a number of ways. The shaft 14 is adapted to be driven by motor 12 such that the shaft 14 describes a helical path, which can be decomposed into circular motion (azimuthal direction) and translational motion (in the direction of longitudinal axis 18). A pitch of the pin thread of the shaft 14 is chosen for adequate motor 12 performance and the manner in which actuable elements of the motor 12 selectively engage the pin thread. Another consideration is a desired amount of translational motion. This may depend on an intended scanning process. For example, if it is desirable to image a particular region (e.g., using Optical Coherence Tomography, Raman spectroscopy, or non-linear optical techniques such as CARS, SERS, SHG, THG, etc.) and to provide a high spatial accuracy map of a lumen in which the catheter is inserted, and if the translational motion of the catheter at the base end is not as accurate as the motor's motion (e.g. if the catheter follows a torturous path), it may be preferable to stabilize the catheter at a single point, and then scan by the continued action of the motor. It may be preferable to stabilize the catheter near the insertion end, for example, by partial inflation of a balloon (or other stabilizer if blocking the lumen is not desired), as may be provided elsewhere on the catheter. In such a case, a pitch p of the pin thread, (i.e. the translational distance per 360° rotation) can be chosen to correspond with a resolution r of the desired image in the longitudinal direction. For example, if n scans are to be averaged to produce the image at each pixel, p=r/n would be a natural choice. If p is much less than the desired longitudinal resolution, scanning of different depths may be performed during respective rotations within a given longitudinal resolution. The higher p is, the slower the actuation, and/or the smaller a resolution in the azimuthal direction. The longer shaft 14 extends (d), the greater the number (d/r) of longitudinal resolution pixel provided on the map and having the higher spatial accuracy. The shaft 14 may retract until mechanically stopped by a stopper (on the threading or at the surface), or as controlled by the motor 12 to minimize the extent of the catheter that is inflexible, during insertion or retraction of the catheter. The length of the shaft 14 may be constrained by limits to flexibility of the catheter given its outer diameter, or the angular inertia which may exceed the rotational support base provided by the covering 10. Alternatively, motion at the catheter base may be used to control the transverse direction.

It will be appreciated that the pin thread on the shaft 14 may be effectively used to secure an end cap for the catheter onto the shaft 14. As the shaft 14 has an outer diameter less than that of the motor 12, tips shown in FIGS. 2a,b do not enlarge the catheter. Nonetheless a wide variety of tips can be used to rigidly secure end caps of different configurations to the shaft 14. While the tips shown use a mirrored surface for reflecting the beam, it will be appreciated that refraction or grating-based surfaces may alternatively be used to form a light path element to redirect light between the longitudinal axis and a direction substantially perpendicular thereto. These may further include actuable members, for example, to permit selective engagement of a mirror for the end cap.

Figure 2A:
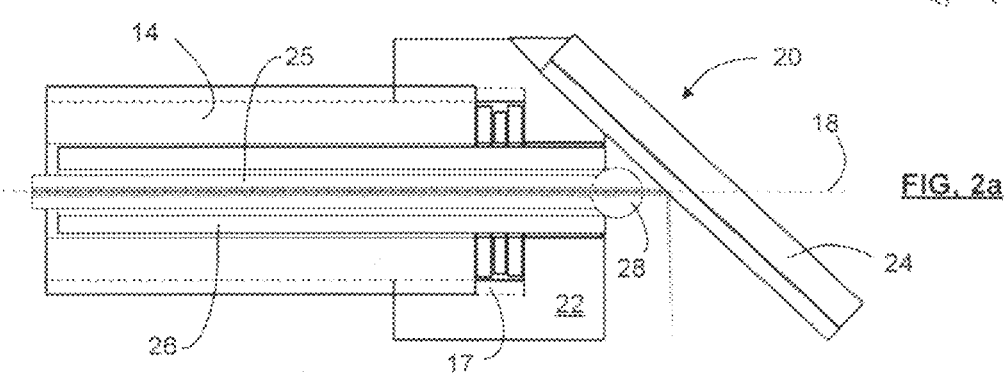
FIGS. 2a,b,c are schematic illustrations of three electromagnetic path elements for coupling to the catheter of FIG. 1.

FIG. 2a schematically illustrates an embodiment of a tip 20 threadedly coupled to shaft 14 of FIG. 1. The tip 20 shown consists of a nut body 22, box threaded 24 to match pin threading of the shaft 14, with a throughbore concentric with the longitudinal axis 18, and a mirror 24, preferably a first surface mirror, rigidly mounted to the nut body 22 for redirecting light between a radial direction and the longitudinal direction. Mirror 24 may be provided in any number of forms, such as: glass ball cleaving, semiconductor etching, and metal plate punching, and commercially available products, such as a micro-prism made by Tower Optical Corp. (Boynton Beach, Fla.). While the mirror 24 is shown mounted along a single side of the nut body 22, it will be appreciated that the mirror 24 could be mounted to the shaft 14 at three sides as only a single side of the tip 20 provides a window for a beam. Naturally the mirror 24 could be replaced with a refractive-based or diffraction-based optical path element. The mirror 24 may be dichroic and the substrate may be transparent, permitting the same optical path to be used at different wavelengths for guidance of the catheter (the beam continuing through the mirror 24 at certain wavelengths substantially along the longitudinal axis 18), and for radial scanning, at wavelengths for which the mirror 24 is reflective to a high degree.

The throughbore of the catheter houses an optical path, which is in the form of a fibre 25, that is clad in a protective steel sheath 26, although it could be otherwise. At a tip of the fibre 25, a ball lens 28 provides for a focusing of the light from the optical fibre 25, and for collecting light reflected from mirror 24. In the present embodiment, the sheath 26 is rotatably mounted to the nut body 22 and shaft 14 via a washer and spacers which effectively retain the sheath 26 axially to the nut body 22, allowing some rotation of the sheath 26. Accordingly, at the end cap, the optical fiber 25 is rotationally free, reducing torsional tension within the fibre. Specifically, the centre washer is solidly connected with sheath 26. When the tip 20 rotates and moves, the head cap pulls or pushes the sheath 26 forward or backward. The two spacers sandwiching the washer are used to reduce the rotating friction, permitting damped rotation of the sheath 26 and fibre 25 together. The sheath 26 is so closely fitting with the fibre 25 that it resists relative movement in terms of rotation and translation, and thus the fibre 25 is locked in motion with the tip 20. Thus the fibre 25 is driven by the tip 20 in the present embodiment, at the insertion end of the catheter, and a constant distance is provided between the ball lens 28 and the mirror 24.

The constant distance between the ball lens 28 and mirror 24 ensures a focusing of a beam through the fibre 25 at a constant radial distance from the axis 18, which is important for stability of the rotationally scanning beam, and the interpretation of the response signal, which may be highly sensitive to phase offset, for example, if interferometric detection is used.

It will be appreciated that, variants of this system are possible. The sealing system may be avoided and the fibre 25, or fibre 25 and sheath 26 together, may be designed to move with little friction within the throughbore of the catheter. The interface between the sheath 26 and nut body 22 and/or the sheath 26 and fibre 25 may be rotational and not translational (telescopically along the longitudinal axis 18), rotational and telescoping, or telescopic and non-rotational. Rotational may be preferred if changing torsion of the fibre 25 introduces artifacts in the signal, and the torturous path of the optical fibre lead to interaction of the covering 10 and fibre 25 that results in excessive torsional stresses. Telescoping connection may be preferred if changing a distance between the ball lens 28 and mirror 24 can be used to intentionally set a different scan depth for the sample. Control over a separation of the ball lens 28 and mirror 24 may be provided at the base of the catheter, or by an additional actuator.

Figure 2B:
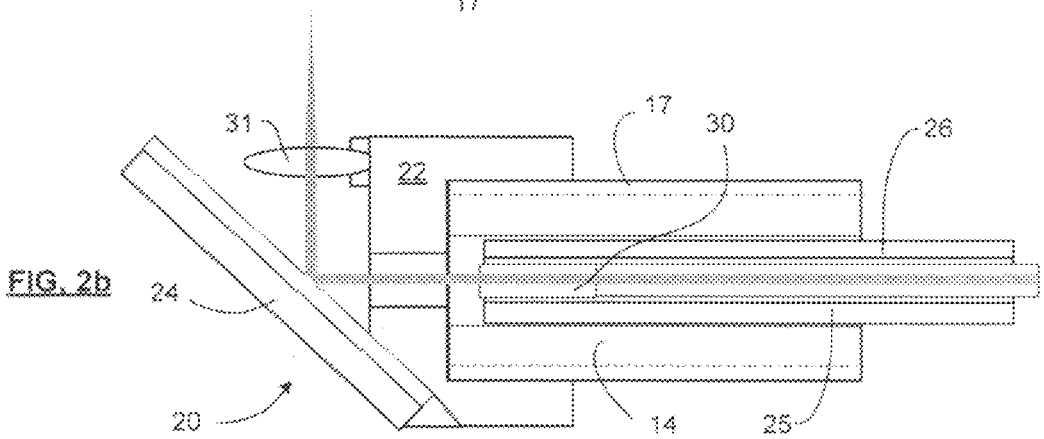

FIG. 2b schematically illustrates another embodiment again having tip 20 with nut body 22, as described in FIG. 2a. Herein features identified by the same reference number denote substantially equivalent elements, and their descriptions are not repeated. The tip 20 of FIG. 2b further comprises a lens 31 (which could alternatively be located before the mirror 24) for focusing light from the fibre 25. Fibre 25, instead of a ball lens, has a collimating tip 30 for issuing a beam in a substantial ray, which reflects off of the mirror 24, and is focused by lens 31. This embodiment makes data much less sensitive to the position of the end of the fibre 25, and provides focusing/collecting optics as close to the sample as possible. The fibre 25 need not be coupled to the shaft 14, but may be coupled to the motor 12 along with the covering 10 to improve a rotational support of the motor 12. Furthermore, as the shaft 14 now drives only the tip 20, and does not grip or twist the fibre 25, an inertial load on the motor 12 is substantially decreased. The fibre and sheath may substantially float within the casing, having no retainers for holding any part at any longitudinal location. Furthermore, given that longitudinal displacements may be much more accurate than torsional displacements, a base end of the fibre may be axially operated to change a focus, angle or other mode of operation of the catheter.

Figure 2C:
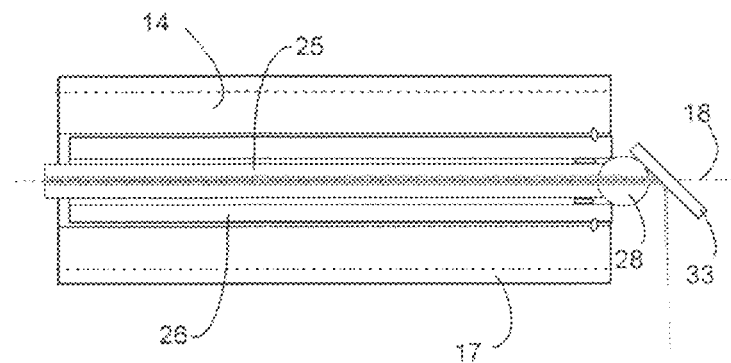

FIG. 2c schematically illustrates a third embodiment wherein the end cap of the longitudinal optical path through the catheter is provided by a snug fitting of the sheath 26 and the shaft 14. As the shaft 14 is shown having a smallest diameter bore, it will be the only section of the throughbore of the catheter to provide gripping contact with the sheath 26. This may be a sealed coupling having an O-ring or elastomeric plug at the shaft/sheath and sheath/fibre interfaces. In the illustrated embodiment a reflector 33 is coupled to the ball lens 28, however the ball lens 28 could be cleaved to provide the reflective surface, or the reflector 33 could equally be affixed to one or more of the sheath 26, shaft 14, and fibre 25 (which could extend beyond the tip of the sheath 26). Driving the fiber at the insertion end of the catheter shares some disadvantages with the base-driven prior art catheters, in that an unknown resistance to the rotation may be encountered, and torsion on the fibre may affect fibre birefringence. Nonetheless a higher accuracy is provided by controlling the fibre at the insertion end, as opposed to at the base end, and various liquid media can be used to mitigate torsional resistance, especially if rotation of the fibre is limited to a few turns.

Other squiggle motors are known in the art that provide rotational (and no axial) motion. Such squiggle motors could alternatively be used. In such cases, it is unnecessary to secure the fibre 25 or sheath 26 to the shaft 14 as required in the embodiment of FIG. 2a, as the distance between the fibre 25 and tip 20 are not expected to change in operation.

EXAMPLES

Figure 3:
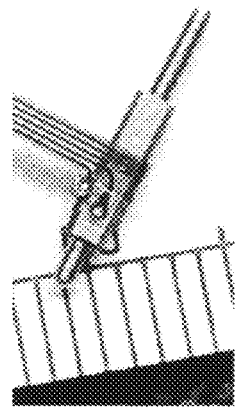
FIG. 3 is an image of a commercially available squiggle motor.

A prototype device has been produced. A commercially available miniature rotary motor, squiggle motor (outer diameter 1.8 mm, as shown in FIG. 3, shaft outer diameter 1.1 mm, thread pitch 0.16 mm) was obtained from New Scale Technologies (Victor, N.Y.). FIG. 3 is an image of the squiggle motor. Other squiggle motors, including some with smaller shaft OD (e.g., 1.5 mm are commercially available). A threaded shaft of the miniature motor was bored to produce a through hole along its centre axis with an inner diameter of 0.4 mm. This proved difficult, but the details are not provided here, as hollow shafts, even of these dimensions, can be provided in a variety of ways known in the art by forming techniques that are expected to be easier than boring an axial hole through a solid shaft as done in the present instance.

A fibre with a protective steel sheath was obtained from (SMF-130V, Prime Optical Fiber Corporation), having an OD of 0.125 mm. The fibre had a ball lens formed thereon by a fusion splicer, FSM-45PM-LDF, Fujikura). A cap as shown in FIG. 1 was produced to mate with the threaded shaft. The tiny mirror was solidly mounted with the motor's rotating screw shaft with a 45° reflecting angle using an epoxy. Washers and spacers were produced. The catheter was assembled by placing the spacer and washers around the tip of the sheathed fibre near the ball lens, inserting the assembly through the shaft (which was in place within the motor), until the ball lens extended a short distance from the threaded shaft, and then the cap was placed over the shaft and screwed into place.

When driving signal was applied to the leads of the motor, which was held in secured against rotation by a mounting, the threaded screw shaft traced a helical path back and forth. Specifically, as per the specifications of the squiggle motor, a 2.5-3.8 V, (operational power 300 mW) DC power supply supplied to leads resulted in longitudinal motion of about 7 mm/s and azimuthal scanning at a rate of 2400 rpm, although various rates can be obtained depending on the applied voltage.

Figure 4A:
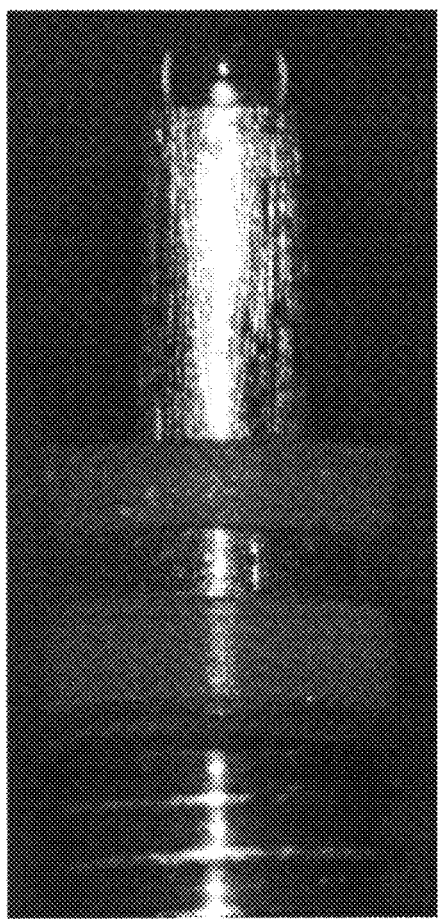
FIGS. 4a,b are images of a prototype catheter with and without an end cap.
Figure 4B:
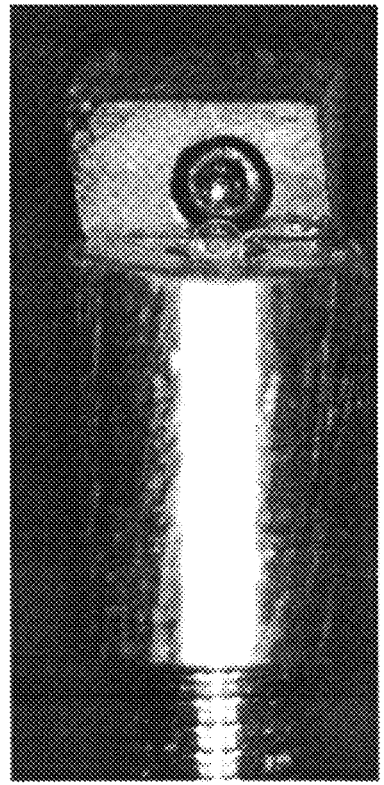

When motor's threaded shaft and mirror rotates, the light emitted from fibre becomes a rotary side-view scanning beam. This device avoids driving rotating of the fibre from the base end, and therefore makes the beam scanning stable and smooth, as is particularly important for high resolution scanning. In addition, because no coupling component is used, it also avoids the light reflection between surfaces in still-rotation convert devices at the base of the catheter, which is very important to the weak signal back scattered from deep structure. FIGS. 4a,b are images of the operating prototype. FIG. 4a shows a ball lens of an optical fibre exiting the threaded shaft, and in FIG. 4b a cap is shown assembled over the threaded shaft, and providing a mirrored surface for reflecting light between radial and longitudinal (i.e. axial) directions.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A catheter comprising:
an electromagnetic path passing longitudinally through a body of the catheter from a base end to an insertion end;
a motor encircling the longitudinal path at the insertion end, the motor anchored to the catheter and having a rotor that extends from the motor, in a direction of insertion,
the rotor coupled to an electromagnetic path element that caps the longitudinal path, to redirect a beam between the longitudinal path and a substantially radial direction, in at least one mode of operation; and
leads for power supply and control of the motor extending to the anchored part of the motor, and not extending beyond the rotor;
wherein the motor drives the rotor to control an azimuthal angle of the radial beam, which is further from the base end than the motor.

2. The catheter of claim 1 wherein the path element is only coupled to the catheter via the rotor.

3. The catheter of claim 1 wherein the motor comprises a plurality of actuable piezoelectric elements secured to the anchoring in a ring around the longitudinal path, the elements adapted to selectively engage the rotor, which is in the form of a cylinder concentrically mounted about the ring.

4. The catheter of claim 1 wherein the motor is a squiggle motor.

5. The catheter of claim 1 wherein the electromagnetic path comprises an optical fibre.

6. The catheter of claim 5 wherein the electromagnetic path element comprises a deflector.

7. The catheter of claim 1 wherein the motor drives the rotor in a circular or helical motion.

8. The catheter of claim 5 wherein the optical fibre extends through the catheter, through the motor, and at least partly into the rotor.

9. The catheter of claim 5 wherein the optical fibre extends through the catheter, through the motor, and completely through the rotor to couple with the path element that caps the electromagnetic path.

10. The catheter of claim 5 wherein the optical fibre has a tip, the tip having at least one of: a lens; a region having a higher OD than a remainder of the optical fibre; a colimating lens; a ball lens and a region that protrudes beyond a protective casing of the optical fibre.

11. The catheter of claim 5 wherein the optical fibre is rotatably mounted to the catheter.

12. The catheter of claim 5 wherein the optical fibre is rotatably mounted to the catheter but retained against longitudinal movement with respect to the catheter.

13. The catheter of claim 12 wherein the optical fibre is retained against longitudinal movement with respect to the catheter at the insertion end.

14. The catheter of claim 12 wherein the optical fibre is retained against longitudinal movement with respect to the catheter at an inner through bore of the rotor.

15. The catheter of claim 5 wherein the optical fibre is retained within the catheter unrestrained with respect to rotation or longitudinal movement of the catheter at the insertion end.

16. The catheter of claim 1 wherein the electromagnetic path element comprises a reflective surface, a refractive surface.

17. The catheter of claim 1 wherein the electromagnetic path element comprises a dichroic mirror for deflecting only some modes along the electromagnetic path.

18. The catheter of claim 16 the electromagnetic path element further comprises a lens.

19. The catheter of claim 18 wherein the lens is located near an OD of the catheter to provide focusing/collecting optics as close to the sample as possible.

* * * * *